United States Patent
Sheppard et al.

(10) Patent No.: US 10,067,129 B2
(45) Date of Patent: Sep. 4, 2018

(54) WIRELESS BASED MARINE PATHOGENS DETECTION SYSTEM

(75) Inventors: Barbara Jane Sheppard, Gainesville, FL (US); Yu-Lin Wang, Taoyuan (TW); Fan Ren, Gainesville, FL (US); Stephen John Pearton, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 827 days.

(21) Appl. No.: 13/319,417

(22) PCT Filed: May 6, 2010

(86) PCT No.: PCT/US2010/033831
§ 371 (c)(1),
(2), (4) Date: Nov. 8, 2011

(87) PCT Pub. No.: WO2010/132263
PCT Pub. Date: Nov. 18, 2010

(65) Prior Publication Data
US 2012/0058488 A1   Mar. 8, 2012

Related U.S. Application Data

(60) Provisional application No. 61/178,766, filed on May 15, 2009.

(51) Int. Cl.
*G01N 33/569* (2006.01)
*G01N 27/414* (2006.01)

(52) U.S. Cl.
CPC ..... *G01N 33/56905* (2013.01); *G01N 27/414* (2013.01); *G01N 27/4145* (2013.01); *Y02A 50/52* (2018.01)

(58) Field of Classification Search
CPC ......... G01N 33/56905; G01N 27/4145; G01N 27/414
See application file for complete search history.

(56) References Cited

U.S. PATENT DOCUMENTS 4,238,757 A * 12/1980 Schenck .................. 257/253
6,485,905 B2 * 11/2002 Hefti ........................ 435/6.11
(Continued)

FOREIGN PATENT DOCUMENTS

WO    WO-2009-039298 A2    3/2009

OTHER PUBLICATIONS

Kang, B., et al., "Electrical detection of biomaterials using AlGaN/GaN high electron mobility transistors," Journal of Applied Physics, 2008, vol. 104, 031101.
(Continued)

*Primary Examiner* — Melanie Yu Brown
(74) *Attorney, Agent, or Firm* — Alston & Bird LLP

(57) ABSTRACT

Embodiments of the present Invention provide antibody functionalized high electron mobility transistor (HEMT) devices for marine or freshwater pathogen sensing. In one embodiment, the marine pathogen can be *Perkinsus marinus*. A sensing unit can include a wireless transmitter fabricated on the HEMT. The sensing unit allows testing in areas without direct access to electrical outlets and can send the testing results to a central location using the wireless transmitter. According to embodiments, results of testing can be achieved within seconds.

11 Claims, 4 Drawing Sheets

(56) References Cited

U.S. PATENT DOCUMENTS

| | | | |
|---|---|---|---|
| 7,403,113 B2 | 7/2008 | Moon et al. | |
| 2002/0137917 A1* | 9/2002 | Vasta et al. | 536/23.7 |
| 2003/0089899 A1* | 5/2003 | Lieber et al. | 257/9 |
| 2005/0224346 A1* | 10/2005 | Holm-Kennedy | 204/403.01 |
| 2005/0263790 A1* | 12/2005 | Moon et al. | 257/194 |
| 2006/0055392 A1 | 3/2006 | Passmore et al. | |
| 2006/0121501 A1* | 6/2006 | Jabs et al. | 435/6 |
| 2006/0141474 A1* | 6/2006 | Miyahara | C12Q 1/6837 435/6.11 |
| 2006/0223170 A1* | 10/2006 | Kamahori et al. | 435/287.2 |
| 2006/0228723 A1* | 10/2006 | Bradley et al. | 435/6 |
| 2006/0246443 A1* | 11/2006 | Bockelmann | C12Q 1/6825 435/29 |
| 2007/0183782 A1 | 8/2007 | Farr et al. | |
| 2008/0032294 A1* | 2/2008 | Kawarada | 435/6 |
| 2008/0184775 A1 | 8/2008 | Yamagishi et al. | |
| 2010/0273672 A1* | 10/2010 | Demoustier-Champagne et al. | 506/9 |
| 2010/0279309 A1* | 11/2010 | Sui | 435/7.1 |

OTHER PUBLICATIONS

Wang H. et al., "Electrical detection of kidney injury molecule-1 with AlGaN/GaN high electron mobility transistors," Applied Physics Letters, 2007, vol. 91, 222101.

Kang, B., et al., "Prostate specific antigen detection using AlGaN/GaN high electron mobility transistors," Applied Physics Letters, 2007, vol. 91, 112106.

Kang, B., et al., "Enzymatic glucose detection using ZnO nanorods on the gate region of AlGaN/GaN high electron mobility transistors," Applied Physics Letters, 2007, vol. 91, 252103.

Kang, B., et al., "Electrical detection of immobilized proteins with ungated AlGaN/GaN high-electron-mobility Transistors," Applied Physics Letters, 2005, vol. 87, 023508.

Kang, B., et al., "Electrical detection of deoxyribonucleic acid hybridization with AlGaN/GaN high electron mobility transistors," Applied Physics Letters, 2006, vol. 89, 122102.

Wang, Y.-L., et al., "Fast detection of a protozoan pathogen, *Perkinsus marinus*, using AlGaN/GaN high electron mobility transistors," Applied Physics Letters, 2009, vol. 94, 243901.

\* cited by examiner

… (1)

WIRELESS BASED MARINE PATHOGENS DETECTION SYSTEM

CROSS-REFERENCE TO RELATED APPLICATIONS

This application is the U.S. national stage application of International Application Ser. No. PCT/US2010/033831, filed May 6, 2010, which claims the benefit of U.S. Provisional Application Ser. No. 61/178,766, filed May 15, 2009, which are hereby incorporated by reference in their entirety, including all figures, tables and drawings.

BACKGROUND OF INVENTION

The World Organization for Animal Health (Office International des Epizooties—OIE) maintains a list of economically important pathogenic organisms responsible for significant damage and devastation to commercial food aquaculture industries, including shellfish, throughout the world. The United States Department of Agriculture (USDA) at both the national and the state level requires periodic mandatory reporting of any confirmed cases of these pathogens within the United States as part of a global cooperative effort to limit the movement of pathogens to previously uninfected areas. For example, the pathogenic protozoa *Perkinsus marinus* (*P. marinus*) and *Perkinsus olseni* (*P. olseni*) are both OIE "reportable" or "notifiable," but the reporting system is intended to prevent their introduction into the Indo-Pacific and North America, respectively. *Perkinsus* species (*Perkinsozoa, Alveolata*) are the causative agents of perkinsosis in a variety of mollusk species. *Perkinsus* species infections cause widespread mortality in both natural and farm-raised oyster populations, resulting in severe economic loss for the shellfish industry and detrimental effects on the environment. In particular, *P. marinus* causes significant mortalities in the economically important Eastern oyster, crossostrea virginica, along the east coast of the United States and the Gulf of Mexico. *Perkinsus olseni* has a broad geographic range extending from the Pacific Ocean around Japan and Eastern Asia to Australia and New Zealand, areas of the European Atlantic and the Mediterranean. The western hemisphere had remained free of *P. olseni*, with the exception of one report in Uruguay until it was discovered in ornamental reef clams, *Tridacna crocea*, legally imported into Florida, USA by the aquatic ornamental trade. The ornamental industry is under increasing scrutiny as the source of introduced exotic pathogens as it is not regulated by the USDA and is not required to test, quarantine, or provide health certificates.

There is growing concern among domestic and international trade partners that the USA is experiencing uncontrolled introduction of serious exotic pathogens through global trade from distant ecosystems in addition to ongoing issues with domestic pathogens impacting aquaculture production and human health. Current testing methods are not performed at the sampling location and require significant delay, expense, and expertise. Owners of saltwater aquaria containing *P. olseni*-infected ornamental clams and water in the USA have no way to test their effluents prior to discharging them into a drainage system or the environment.

Current testing methods for aquatic pathogens require transport of sampling material to a testing location. The commonly used methods require several days and include growing the organism in specialized media, detection with specialized molecules, or purification of genetic material followed by molecular testing. Currently, the standard diagnostic method for *Perkinsus* species infections has been the Fluid Thioglycollate Medium (FTM) assay detection. However, it takes several days to do the detection using this method. The polymerase chain reaction (PCR)-based technique is also used to diagnose *Perkinsus*, but it is quite expensive and time-consuming, and requires exquisite controls to assure specificity and accuracy. Clearly, such methods are slow and impractical to be used in the field. Furthermore, these methods require a dedicated testing location and staff and significant specialized training. In addition, they require a variety of expensive instrumentation and reagents, and involve multiple steps with potential failure at many stages. Replication in duplicate or triplicate is often necessary, which increases the time and costs.

Thus, there exists a need in the art for improved monitoring and regulation of aquatic pathogens for the aquatic industries, research, and home use.

BRIEF SUMMARY

Embodiments of the present invention relate to field-deployable electronic biological sensors utilizing functionalized high electron mobility transistors (HEMTs). In a specific embodiment, the HEMT sensors can he used for the on-site detection of marine pathogens such as *Perkinsus marinus*.

According to an embodiment of the invention, a gate area of a HEMT can be functionalized with marine or freshwater pathogen antibody/antigen. In a specific embodiment, an antibody-functionalized Au-gated AlGaN/GaN HEMT can be used for detecting *Perkinsus marinus*.

The subject system can provide a reading within moments, enabling an operator the immediate opportunity to assess whether additional testing should be done in that or other areas. The subject system can include a portable or embedded power supply, allowing testing in areas without direct access to an electrical outlet. In addition, a wireless transmitter can he incorporated in the system, allowing test results to be communicated to a receiving location. A centralized receiving location can be utilized in conjunction with multiple sensor systems.

In accordance with an embodiment of the present invention, a marine pathogen sensor can be provided to an average nonscientist operator for easy, rapid, on-site detection of an organism.

DETAILED DISCLOSURE

Figure 1:
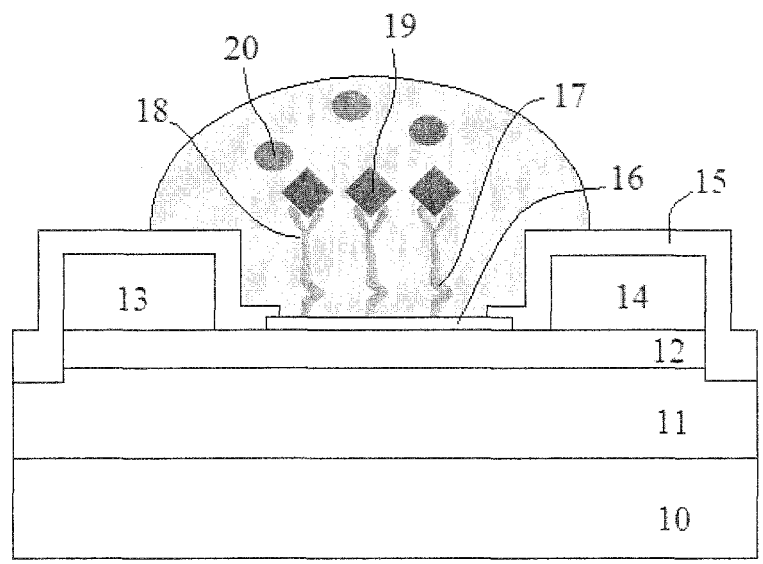
FIG. 1 shows a cross-sectional view of a HEMT sensor having an anti-*P. marinus* antibody functionalized gate area according to an embodiment of the present invention.

Embodiments of the present invention relate to a pathogens detection system using a high electron mobility transistor (HEMT) capable of performing as a marine or freshwater pathogen sensor.

Embodiments of the present invention have the capability for reliable, inexpensive, highly sensitive, hand-held sensors with response times on the order of a few seconds, which can be used in the field for detecting marine or freshwater pathogens.

According to embodiments, on-site testing of samples at the point of commerce, research or residence can be achieved. The subject sensor can provide a reading within seconds, which allows an operator of the sensor the immediate opportunity to assess whether additional testing should be performed. The immediate results at the location of the operator's choice eliminate the delay required for sample transportation or mailing in addition to the 2-10 days required for other diagnostic assays.

The small size of the sensor makes it readily mobile to another location within the same or another facility and it is readily transported in watercraft and vehicles. The sensor can be wireless, allowing testing in areas without direct access to an electrical outlet, and can send the testing results to a central location. The central location can receive signals from one or more remotely deployed sensor systems.

According to an embodiment, the subject sensor can use a chip capable of repeated readings.

In addition, the overall testing method used by the subject sensor can eliminate or substantially reduce the need for numerous laboratory disposables and solutions required for the other techniques. The sensing unit can also eliminate or substantially reduce the need for laboratory biohazard disposal protocols and associated regulatory oversight and expenses which are inherent to the other testing methods. The cost of operation can be a fraction of the current methods given the lack of dedicated laboratory space and personnel, reagents, disposables, biohazard disposal, and sample transportation or mailing.

According to embodiments, the subject system can incorporate multiple sensors on a single chip. The single chip can provide multiple sensors functionalized with different kinds of antibodies in order to test for a variety of marine or freshwater pathogens.

According to embodiments of the present invention, the subject sensors can utilize III-V based HEMTs. For example, the subject sensors can utilize HEMTs such as AlGaN/GaN HEMTs, AlGaAs/GaAs HEMTs, InGaP/GaAs HEMTs, and InAlAs/InGaAs HEMTs. In further examples, the subject sensors can utilize HEMTs such as AlGaAs/InGaAs PHEMTs, InAlAs/InGaAs PHEMTs, Sb based HEMTs, and InAs based HEMTs.

The AlGaN/GaN HEMT is an exemplary HEMT that can be used for marine pathogen sensing. AlGaN/GaN HEMTs have high electron sheet carrier concentration channel induced by piezoelectric polarization of the strained AlGaN layer. Electrons in the two-dimensional electron gas (2DEG) channel are located at the interface between the AlGaN layer and GaN layer. In addition, there are positive counter charges at the HEMT surface layer induced by the electrons located at the 2DEG channel. Slight changes in the ambient can affect the surface charge of the HEMT, thus changing the 2DEG concentration in the channel. This operation works similarly in the AlGaAs/GaAs HEMT, InGaP/GaAs HEMT, and InAlAs/InGaAs HEMT (and other HEMTs) at the interface between the dual layer structures.

HEMTs can operate over a broad range of temperatures and form the basis of next-generation microwave communication systems. Accordingly, embodiments of the present invention can be implemented as an integrated sensor/wireless chip by incorporating wireless transmission circuitry on the same chip as the sensors. In addition, a portable or embedded power supply can be included. The power supply can be, for example, a battery or other power source.

Embodiments utilizing the HEMT sensor can provide a fast response time. In a further embodiment, the subject device can be used as a wireless based sensor to send testing results to a display or separate device.

Referring to FIG. 1, a *P. marinus* sensor can include an HEMT grown on a substrate 10. The substrate can be, for example, silicon, sapphire, or SiC substrate. In one embodiment, epi-layers for the HEMT (e.g., GaN 11 and AlGaN 12 layers for an AlGaN/GaN HEMT) can be grown by molecular beam epitaxy (MBE) on the sapphire or SiC substrate 10. In another embodiment, the epi-layers can be grown by metal organic chemical vapor deposition (MOCVD) on the silicon, sapphire, or SiC substrate 10. Source and drain electrodes 13 and 14 can be formed on the HEMT and an electrode 16 can be formed on the gate region of the HEMT. A protective coating 15 can be formed exposing the gate region.

A coating of anti-*P. marinus* antibody 18 can be provided on the electrode 16. The antibody 18 is selective to its corresponding antigen 19 such that mismatched antigen 20 in the solution in contact with the sensor will not attach. Antibodies are protein molecules that are composed of equal numbers of heavy and light polypeptide amino acid chains held together with disulfide bonds. These highly specialized proteins are able to recognize and bind selectively certain types of antigen molecules. The antibodies or other capture reagents for a target molecule are attached to a gate region of an HEMT for sensing applications.

The electrode 16 can include a gold (Au) thin film. The gold surface of the gate electrode 16 can optionally be functionalized with a bi-functional molecule, such as thioglycolic acid 17 (TGA; $HSCH_2COOH$ containing a thiol (mercaptan) and a carboxylic acid functional group) before coating with the anti-*P. marinus* antibody 18. The thioglycolic acid can be immobilized by the strong interaction between the gold and the thiol-group of the thioglycolic acid.

Other antibody binding agents, such as cysteamine ($NH_2CH_2CH_2SH$), 1,2-ethanedithiol ($HSCH_2CH_2SH$), dimercaprol (BAL), diaminoethanetetraacetic acid (EDTA), 2,3-bis-sulfanylbutanedioic acid (DMSA), or 2,3-dimercapto-1-propanesulfonic acid (DMPS) can be utilized in certain embodiments.

In operation, any slight changes of the surface charges in the ambient of the HEMT' affect the surface charges on the AlGaN/GaN. These changes in the surface charge are transduced into a change in the concentration of the 2DEG in the AlGaN/GaN HEMTs, leading to the decrease in the conductance for the device after exposure to *P. marinus*-infected water.

A HEMT with the anti-*P. marinus* antibody/antigen on thioglycolic acid functionalized Au-coated gate area can exhibit noticeable changes in the surface charges upon exposing the gate region to *P. marinus*. According to certain embodiments, the detection time for the HEMT based sensor can be in the range of 5-20 seconds (see e.g., FIGS. 4, 5A and 5B).

Embodiments of the present invention can use utilize the above described electrical response to provide a marine pathogen or freshwater pathogen sensing device.

In addition to *Perkinsus* species pathogens, other marine and freshwater pathogens can be detected using pathogen specific antibodies. Examples of pathogens contemplated within the scope of the invention, include, but are not limited to, *Aeromonas caviae, Aeromonas hydrophila, Aeromonas salmonicida, Aeromonas sobria, Flavobacterium psychrophilum, Listonella anguillarum, Listonella pelagia, Photobacterium damselae, Photobacterium leiognathi, Photobacterium phosphoreum, Streptococcus parauberis, Tanacibaculum maritimum, Vibrio aestuarianus, Vibrio alginolyticus, Vibrio cholerae, Vibrio fischeri, Vibrio harveyi, Vibrio metschnikovi, Vibrio natriegens, Vibrio nereis, Vibrio ordalii, Vibrio parahaemolyticus, Vibrio splendidus, Vibrio tubiashii,* and *Vibrio vulnificus.*

According to an embodiment, depending on the specificity of the antibody functionalizing the device, qualitative tests can be performed to determine if the existence of one or more of multiple species of pathogens exist in a sample.

Although an AlGaN/GaN HEMT is described as the HEMT for use in the aforementioned embodiments, other HEMTs, including, but not limited to, an AlGaAs/GaAs HEMT, an InGaP/GaAs HEMT or an InAlAs/InGaAs HEMT can be used in place of the AlGaN/GaN HEMT.

In one embodiment, multiple sensors can be fabricated on a single chip by forming a plurality of HEMTs and then individually functionalizing each HEMT for a particular sensing application using any known masking techniques. Other circuitry can also be included. For example, a wireless transmitter and related circuitry can be fabricated on the substrate.

Figure 2:
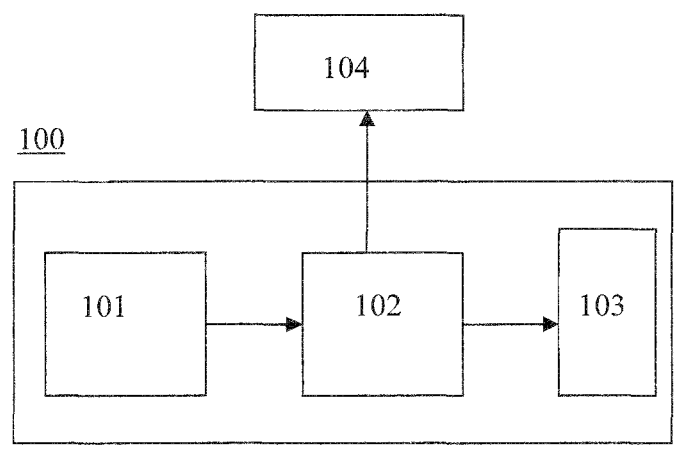
FIG. 2 shows a functional block diagram of a marine pathogen sensing system according to an embodiment of the present invention.

According to an embodiment, as shown in FIG. 2, a marine or freshwater pathogen sensing device 100 can include a sensor region 101 that communicates to a processing region 102, which in turn communicates to an antenna 103 for wireless transmission of the signals. The processing region 102 can be primarily for wireless transmission control or can include additional functionality. For example, in implementations utilizing additional functionality, the functionality can include circuitry capable of analyzing the signals from the sensor region 101. In a further embodiment, output of the sensor region 101 can be provided to a display device 104 connected to the marine or freshwater pathogen sensing device.

In the field, a sample of water being tested can be applied to the sensor region 101. For example, a pipette can be used to apply the sample to the sensor region 101. In certain embodiments, the sensor region 101 can be at least partially submerged in the water being tested. In such embodiments, elements of the sensing device 100 can be protected using, for example, a waterproof packaging or protective films. The detection of marine or freshwater pathogens can be monitored at the site of the testing by an output (such as visual and/or audio) of the sensing device 100. The monitoring can be accomplished on-site through transmission of data from the antenna of the device to, for example, a computer separate from the sensing device 100. The monitoring can also be accomplished off-site through the transmission of the data to a system located off-site.

A greater understanding of the present invention and of its many advantages may be had from the following examples, given by way of illustration. The following examples are illustrative of some of the methods, applications, embodiments and variants of the present invention. They are, of course, not to be considered in any way limitative of the invention. Numerous changes and modifications can be made with respect to the invention.

EXAMPLES

The HEMT structures used for the following examples have a 3 μm thick undoped GaN buffer, a 30 Å thick $Al_{0.3}Ga_{0.7}N$ spacer, and a 220 Å thick Si-doped $Al_{0.3}Ga_{0.7}N$ cap layer. Here, the epi-layers were grown by a molecular beam epitaxy system (MBE) on sapphire substrates. Mesa isolation was performed by an Inductively Coupled Plasma (ICP) etching with $Cl_2$/Ar based discharges at −90 V dc self-bias, ICP power of 300 W at 2 MHz and a process pressure of 5 mTorr. Ohmic contacts, each having an area of $10 \times 50$ μm$^2$ and separated with gaps of 5 μm, were formed of e-beam deposited Ti/Al/Pt/Au patterned by lift-off. The contacts were annealed at 850° C. for 45 sec under flowing $N_2$. A thin layer of Au was deposited on the gate region. A 400-nm-thick 4% Poly(methyl methacrylate) (PMMA) was used to encapsulate the source/drain regions, with only the gate region open to allow the liquid solutions to cross the surface.

The Au gated surface of the HEMT was functionalized with thioglycolic acid. A self-assembled monolayer of thioglycolic acid, $HSCH_2COOH$, an organic compound and containing both a thiol (mercaptan) and a carboxylic acid functional group, was anchored on the Au surface in the gate area through strong interaction between the gold and the thiol-group of the thioglycolic acid. The device was incubated in a phosphate buffered saline (PBS) solution of 200 μg/ml anti-*P. marinus* rabbit antibody for 18 hours before real time measurement of the infected waters.

The anti-*P. marinus* rabbit antibody was obtained by inoculating rabbits with *P. marinus* and creating a serum-derived polyclonal mixture of the anti-*P. marinus* rabbit antibodies. Though *P. marinus* is the focus of these examples, the anti-*P. marinus* rabbit antibody used in these examples can also recognize many *Perkinsus* species in addition to *P. marinus*.

Also contemplated within the scope of the present invention are antigen binding fragments of antibodies. Fragments of antibodies can be prepared using standard methods known in the art.

In addition, antibodies specific to other marine or freshwater pathogens can be utilized with the present invention to detect those other pathogens. Accordingly, the application of these sensors should not be considered as being limited only to detection of *P. marinas*. In addition, the antibodies, such as anti-*P. marinas* antibodies (or anti-*Perkinsus* sp. antibodies), can be provided in monoclonal or polyclonal forms.

Figure 3:
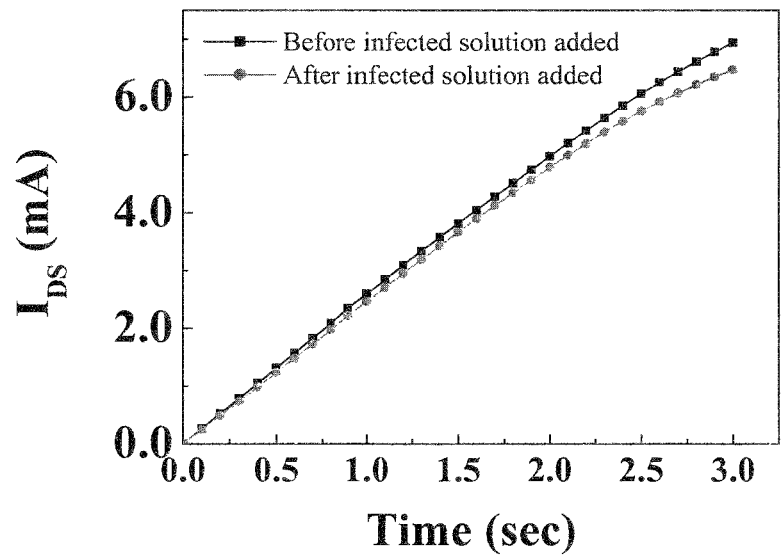
FIG. 3 shows a plot of I-V characteristics of an AlGaN/GaN HEMT sensor according to an embodiment of the present invention before and after exposure to *P. marinus*-infected water from tank 1.

After immobilizing the anti-*P. marinas* rabbit antibody on the gate area of the AlGaN/GaN HEMT sensor, the sensor surface was thoroughly rinsed off with PBS and dried by a nitrogen blower. FIG. 3 shows a plot of I-V characteristics of the HEMT before and after exposure to *P. marinas*. The source-drain current-voltage characteristics were measured at 25° C. using an Agilent 4156C parameter analyzer with the gate region exposed. For the *P. marinas* detection, the drain current of the HEMT sensor was measured at a constant drain bias voltage of 500 mV before and after the sensor was exposed to the water from a first tank (tank 1). Tank 1 included clams (*Tridacna crocea*) that were dead due to *P. marinas* exposure. Any slight changes in the ambient of the HEMT affect the surface charges on the AlGaN/GaN. These changes in the surface charge are transduced into a change in the concentration of the 2DEG in the AlGaN/GaN HEMTs, leading to the decrease in the conductance for the device after exposure to *P. marinus*-infected water.

Figure 4:
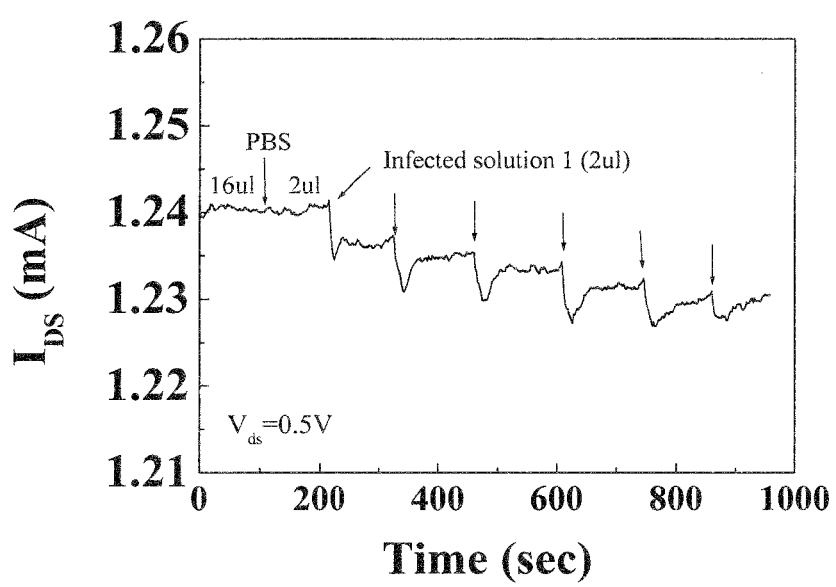
FIG. 4 shows a plot of drain current of an AlGaN/GaN HEMT sensor according to an embodiment of the present invention versus time for *P. marinus* detection in the infected water from tank 1.

FIG. 4 shows a real time *P. marinas* detection using the source and drain current change with constant drain bias of 500 mV. Effectively no current change can be seen with the addition of buffer solution at around 100 seconds, showing the specificity and stability of the device. In clear contrast, the current change showed a rapid response in less than 5 seconds when 2 µl of tank 1 water was added to the surface. The abrupt drain current change due to the exposure of *P. marinus* in a buffer solution was stabilized after the antigen thoroughly diffused into the buffer solution. Continuous 2 µl of the tank 1 water added into a buffer solution resulted in further decreases of drain current. Thus, according to this example, in tank 1, clams died and some of *P. marinas* cells also died and released the specific antigens that were detected by the sensors.

Figure 5A:
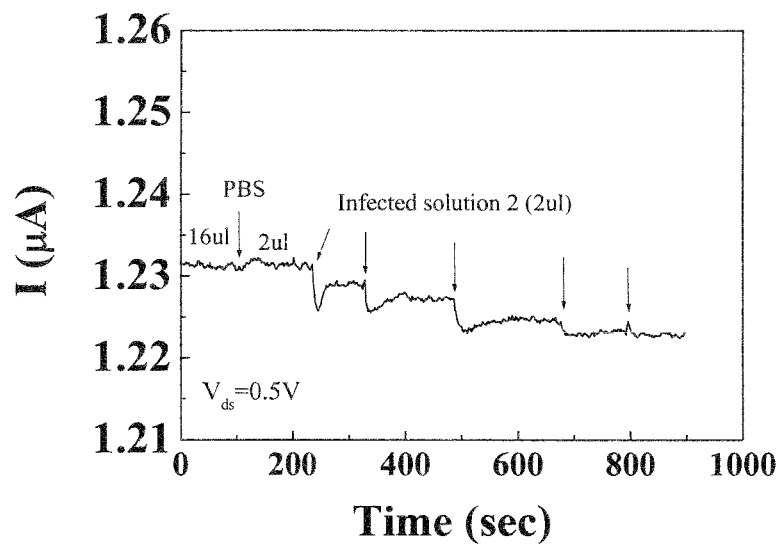
FIGS. 5A and 5B show plots of drain current over time of a *P. marinus* sensor according to an embodiment of the present invention for real-time detection of *P. marinus* in an infected water from tank 2 before (FIG. 5A) and after (FIG. 5B) recycling the sensor with PBS wash.
Figure 5B:
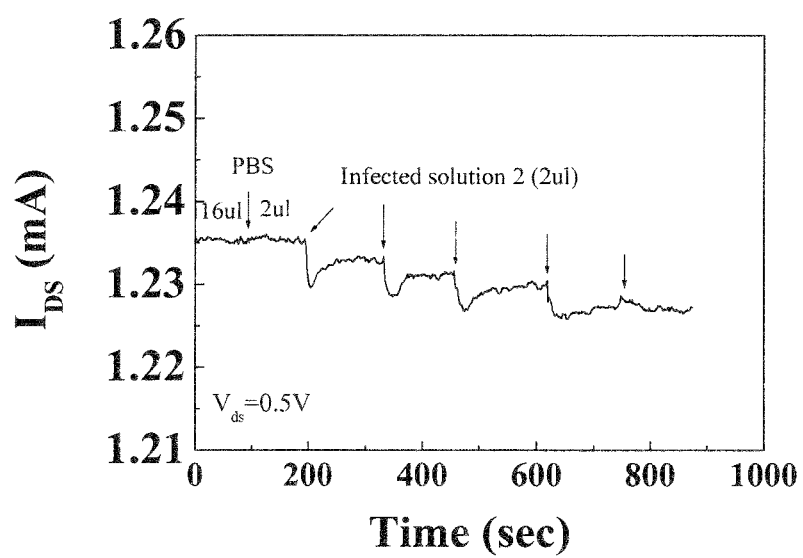

FIG. 5A shows a real time test of *P. marinas* in the water from a second tank (tank 2), in which the clams also died. The abrupt drain current change due to the exposure of *P. marinas* was observed as with the previous experiment shown in FIG. 4. Then, the sensor was washed with PBS (pH 6.5) and used to detect the *P. marinas* again. As shown in FIG. 5B, the recycled sensor still shows very good sensitivity as compared to the original tests. These results demonstrated the real-time *P. marinas* detection and reusability of the sensor.

Figure 6:
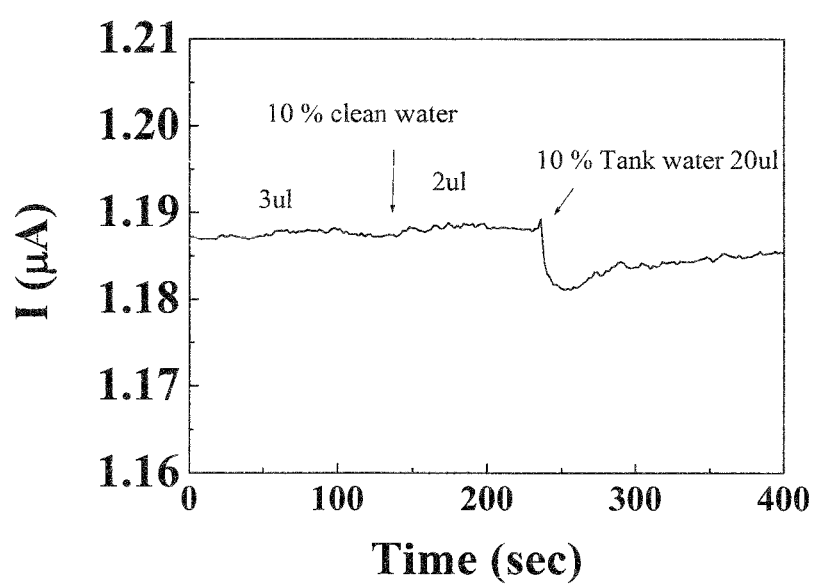
FIG. 6 shows a plot of drain current of an AlGaN/GaN HEMT sensor according to an embodiment of the present invention versus time for *P. marinus* detection in the infected water from tank 1 and fresh artificial seawater without *P. marinus*.

FIG. 6 shows a real time *P. marinas* detection using the source and drain current change with constant drain bias of 500 mV starting with fresh artificial sea water instead of PBS solution as provided in the example shown with respect to the plot of FIG. 4. Effectively no current change can be seen with the addition of diluted sea water, showing the specificity and stability of the device. In contrast, the current change showed a rapid response in less than 5 seconds when 20 µl of tank 1 water was added to the surface. Though there was interference from the artificial sea water, the sensor was sensitive enough to use diluted tank 1 water.

In summary, through a chemical modification method, the Au-gated region of an AlGaN/GaN HEMT structure can be functionalized for direct detection of *P. marinus* in infected waters.

This electronic detection of biomolecules is a significant step towards a field-deployed sensor chip, which can be integrated with a commercial available wireless transmitter to realize a real-time, fast response and high sensitivity *P. marinus* detector.

Accordingly, examples of embodiments of the invention are provided below. These examples should not be construed as limiting.

1. A marine or freshwater pathogen detection system, comprising:
a high electron mobility transistor (HEMT) marine or freshwater pathogen sensor on a substrate; and
a wireless transmitter on the substrate and connected to the HEMT marine or freshwater pathogen sensor for transmitting output of the HEMT marine or freshwater pathogen sensor from a testing location to a receiving location.

2. A marine or freshwater pathogen detection system as in embodiment 1, further comprising a signal controller connected to the output of the HEMT marine or freshwater pathogen sensor and capable of controlling the wireless transmitter. In a further embodiment, the HEMT marine pathogen sensor, the wireless transmitter, and signal controller are fabricated on the same substrate.

3. A marine or freshwater pathogen detection system as in embodiment 2, further comprising a display device connected for receiving output of the HEMT marine or freshwater pathogen sensor through the signal controller in order to display the output of the HEMT marine or freshwater pathogen sensor at the testing location.

4. A marine or freshwater pathogen detection system according to embodiment 1, wherein the HEMT marine or freshwater pathogen sensor comprises a marine or freshwater pathogen specific antibody on a gate region of a HEMT, a source electrode connected to a power signal, and a drain electrode connected to an output line, wherein the wireless transmitter receives the output of the HEMT marine or freshwater pathogen sensor through the output line.

5. A marine or freshwater pathogen detection system as in embodiment 4, further comprising an embedded power supply for providing the power signal to the source electrode.

6. A marine or freshwater pathogen detection system as in embodiment 4, further comprising a portable power supply for providing the power signal to the source electrode.

7. A marine or freshwater pathogen detection system as in embodiment 4, further comprising a binding agent disposed on the gate region of the HEMT to link the marine or freshwater pathogen specific antibody to the gate region of the HEMT. In an embodiment, the binding agent comprises thioglycolic acid. In one such embodiment, the system further comprises a layer of gold at a surface of the gate region, wherein the thioglycolic acid is anchored to a surface of the layer of gold.

8. A marine or freshwater pathogen detection system as in embodiment 4, wherein the marine or freshwater pathogen specific antibody comprises anti-*P. marinus* antibody.

9. A method of detecting a marine or freshwater pathogen, comprising:
allowing a gate region of a high electron mobility transistor (HEMT) marine or freshwater pathogen sensor to contact water being tested; and
monitoring drain current of the HEMT marine or freshwater pathogen sensor to determine presence of marine or freshwater pathogens, wherein a change in drain current occurs upon exposure to marine or freshwater pathogen-infected water;

10. A method as in embodiment 9, wherein monitoring the drain current comprises wirelessly transmitting a signal representing the drain current to a receiving location.

11. A method as in embodiment 9, wherein monitoring the drain current comprises communicating a signal representing the drain current to a display device connected to the HEMT marine or freshwater pathogen sensor.

12. A method as in embodiment 9, wherein the HEMT marine or freshwater pathogen sensor comprises:
a HEMT on a substrate;
a binding agent disposed on the gate region of the HEMT; and
a marine pathogen specific antibody linked by the binding agent to the gate region of the HEMT.

13. A method as in embodiment 12, wherein the binding agent comprises thioglycolic acid. In one such embodiment, the HEMT marine or freshwater pathogen sensor further comprises a layer of gold at a surface of the gate region, wherein the thioglycolic acid is anchored to a surface of the layer of gold.

14. A method as in embodiment 12, wherein the marine or freshwater pathogen specific antibody comprises anti-*P.*

*murinus* antibody, wherein the change in the drain current of the HEMT occurs upon exposure of the gate region of the HEMT to *P. marinus*-infected water.

15. A method as in embodiment 9, further comprising rinsing the HEMT marine pathogen sensor with phosphate buffered saline solution before allowing the gate region of the high electron mobility transistor (HEMT) marine pathogen sensor to contact water being tested.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A method of detecting a marine or freshwater pathogen, comprising:

contacting a gate region and a protective layer of a high electron mobility transistor (HEMT) marine or freshwater pathogen sensor with water being tested;

applying a constant drain bias to the HEMT marine or freshwater pathogen sensor;

monitoring a drain current of the HEMT marine or freshwater pathogen sensor for a change in drain current while the constant drain bias is applied to determine a presence or absence of marine or freshwater pathogens;

analyzing a signal of the drain current; and providing an output of the HEMT marine or freshwater pathogen sensor to a display device, wherein the HEMT marine or freshwater pathogen sensor is configured such that a change in drain current while the constant drain bias is applied and the gate region is contacted with the water being tested indicates that the marine or freshwater pathogen is present in the water being tested, and wherein the protective layer directly covers an epi-layer, a source electrode, and a drain electrode of the HEMT marine or freshwater pathogen sensor while exposing the gate region of the HEMT marine or freshwater pathogen sensor.

2. The method according to claim 1, further comprising repeating the contacting of the gate region of the HEMT marine or freshwater pathogen sensor with water being tested.

3. The method according to claim 2, further comprising rinsing the HEMT marine or freshwater pathogen sensor with a phosphate-buffered saline solution before repeating the contacting of the gate region of the HEMT marine or freshwater pathogen sensor with water being tested.

4. The method according to claim 1, wherein contacting the gate region of the HEMT marine or freshwater pathogen sensor with water being tested comprises applying a sample of the water being tested to the HEMT marine or freshwater pathogen sensor.

5. The method according to claim 1, further comprising incubating the HEMT marine or freshwater pathogen sensor in a phosphate-buffered saline solution prior to contacting the gate region of the HEMT marine or freshwater pathogen sensor with water being tested.

6. The method according to claim 1, wherein contacting the gate region of the HEMT marine or freshwater pathogen sensor with water being tested is done by using a pipette or by submersion.

7. The method according to claim 1, wherein the HEMT marine or freshwater pathogen sensor comprises a plurality of HEMTs on a single chip, wherein each HEMT of the plurality of HEMTs is functionalized for a particular sensing application, and wherein the plurality of HEMTs senses different pathogens at the same time.

8. The method according to claim 7, wherein the HEMT marine or freshwater pathogen sensor further comprises:

a binding agent disposed on the gate region of a HEMT of the plurality of HEMTs; and at least one capture reagent for a marine or freshwater pathogen linked by the binding agent to the gate region of said HEMT.

9. The method according to claim 8, wherein the binding agent comprises thioglycolic acid anchored to a surface of a layer of gold on the gate region of said HEMT.

10. The method according to claim 8, wherein the at least one capture reagent comprises anti-P. marinus antibody, wherein the change in the drain current of said HEMT occurs upon exposure of the gate region of said HEMT to P. marinus-infected water.

11. The method according to claim 1, further comprising transmitting the analyzed signal by wireless transmission.

* * * * *